United States Patent [19]

Hasegawa et al.

[11] 4,189,472

[45] Feb. 19, 1980

[54] ANTIBIOTIC C-11924 F-1

[75] Inventors: Toru Hasegawa, Kawanishi; Mitsuko Asai; Kazunori Hatano, both of Takatsuki, all of Japan

[73] Assignee: Takeda Chemical Industries, Ltd., Osaka, Japan

[21] Appl. No.: 870,085

[22] Filed: Jan. 17, 1978

[30] Foreign Application Priority Data

Jan. 24, 1977 [JP] Japan .................................. 52-7026

[51] Int. Cl.² ............................................. A61K 35/00
[52] U.S. Cl. ................................... 424/117; 435/130; 435/908
[58] Field of Search ................ 424/117; 195/80 R, 80

[56] References Cited

U.S. PATENT DOCUMENTS 3,814,796  5/1974  Argoudelis et al. ................. 424/117

*Primary Examiner*—Jerome D. Goldberg
*Attorney, Agent, or Firm*—Wenderoth, Lind & Ponack

[57] ABSTRACT

A novel Antibiotic C-11924 F-1 is produced by cultivating a microorganism belonging to the genus Streptoverticillium and capable of producing Antibiotic C-11924 F-1 in a culture medium, causing the microorganism to accumulate Antibiotic C-11924 F-1 in the cultured broth and recovering the same therefrom.

Antibiotic C-11924 F-1 is useful for a germicide or disinfectant.

2 Claims, 3 Drawing Figures

ANTIBIOTIC C-11924 F-1

This invention relates to a novel antibiotic C-11924 F-1 and a method for the production thereof.

In search of novel antibiotics, we isolated microorganisms from a large number of soil samples and separated and examined the antibiotics elaborated by such microorganisms. As a result, we found that certain of those microorganisms elaborate a novel antibiotic, that those microorganisms belong to the genus Streptoverticillium and that, when cultivated in an appropriate medium, such microorganisms accumulate said antibiotic in the cultured broth. We designated this antibiotic "Antibiotic C-11924 F-1".

Antibiotic C-11924 F-1 (hereinafter referred to briefly as C-11924 F-1) producing strain, as aforesaid, belongs to the genus *Streptoverticillium*. *Streptoverticillium cinnamoneum* No. C-11924 (hereinafter referred to briefly as Strain No. C-11924) which we isolated from a soil sample obtained at Gero, Gifu Prefecture, Japan is one of the microorganisms which can be most advantageously utilized in the method of this invention. The above strain of microorganism has been deposited at the Institute for Fermentation, Osaka under the accession number of IFO 13713, at the Fermentation Research Institute of the Agency of Industrial Technology under receipt number 3837 of written request for the deposition, and at the American Type Culture Collection, U.S.A. under the accession number of ATCC-31364. The microbiological characteristics of Strain No. C-11924 as investigated by Sherling & Gottlieb's method (International Journal of Systematic Bacteriology, Vol. 16, p. 313–340, 1966) for 3 weeks are as follows.

(1) Morphological characters

Sporulated hyphae in whorls. Cylindrical or phalanx-shaped spores (0.5–0.7×0.9–1.1μ) are produced; smooth surfaces.

(2) Cultural characteristics

This strain produces a cottony or velvety aerial mycelium, whitish-yellow, pinkish gray to pinkish purple gray. The substrate mycelium is yellow to yellowish tan, and substantially no soluble pigments are produced. No production of melanoid pigments.

The cultural characters, physiological characters and carbon assimilation spectrum of this strain are shown in Tables 1 to 3, respectively.

Table 1

Cultural characteristics on various media

| Medium | Reverse color of substrate mycelium | Surface color of substrate mycelium | Growth on surface of colony, and its color | Soluble pigment |
|---|---|---|---|---|
| Sucrose nitrate agar | Colorless | Colorless | Sparse, light pink (4 ca) | None |
| Glucose asparagine agar | Light yellow(2 ea)- dull yellow orange (3 ic) | Light yellow (2 ea)- dull yellow orange (3 ic) | Abundant, white with a tinge of bright brownish gray(3 ec) | None |
| Glycerol-asparagine agar | Light yellow(2 ga)- dull yellow(2 ic) | Light yellow(2 ga)- dull yellow(2 ic) | Moderate, limited growth, beige with a tinge of pink(4 ec) | None |
| Inorganic salts-starch agar | Light yellow(2 ga) | Light yellow(2 ga) | Velvety abundant growth, beige with a tinge of pink(4 ec) | None |
| Tyrosine agar | Light yellow(2 ca)- yellowish tan(3 ne) | Light yellow(2 ca)- yellowish tan(3 ne) | Moderate growth, creased and limited; whitish to yellow | None |
| Nutrient agar | Brown(4 ni)-dark tan | Brown (4 ni) | (Moderate, bright brownish gray(3 ec) | None |
| Yeast extract-malt extract agar | Yellowish orange (3 nc) to yellowish brown (3 ne) | Yellowish orange (3 nc) to yellowish brown (3 ne) | Velvety, good growth, bright brownish gray (3 ec) | None |
| Oatmeal-agar | Dull yellow(2 lc) | Dull yellow(2 lc) | Velvety, good growth, bright brownish gray (3 ec)(3 cb) | None or very light yellowish brown |

The parenthesized symbols indicate the color codes according to Color Harmony Manual, 4th ed. (Container Corporation of America, 1958).

Table 2

Physiological characteristics

| | |
|---|---|
| Temperature range for growth | 10°–40° C. |
| Liquefaction of gelatin | Positive |
| Hydrolysis of starch | Positive |
| Coagulation of skimmed milk | Negative |
| Peptonization of skimmed milk | Positive |
| Production of melanoid pigments | |
|   I) Tyrosine agar | Negative |
|   II) Peptone-yeast extract iron agar | Negative |
| Reduction of nitrates | Negative |

Table 3

Assimilation of carbon sources

| | Growth |
|---|---|
| L-arabinose | ± |
| D-xylose | ± |
| D-glucose | +++ |
| D-fructose | + to ++ |
| D-galactose | + |
| D-trehalose | +++ |
| Sucrose | ± |
| L-rhamnose | ± |
| Raffinose | ± |
| i-Inositol | +++ |
| D-mannitol | ± |
| Control (not added) | ± |

+++: Luxuriant growth
+: Growth
++: Good growth
±: Poor growth
—: No growth

Comparison of the above-described characteristics with the corresponding descriptions in S.A. Waksman's The Actinomycetes, Vol. 2, 1961, The Williams and Wilkins Company; E.B. Scherling and D. Gottlieb's reports in International Journal of Systematic Bacteriology 18, 69 (1968), do. 18, 279 (1968), do. 19, 391 (1969) and do. 22, 265 (1972); R. Locci et al's report in Giornale di Microbiologia 17, 1-60 (1969); and Bergey's Manual of Determinative Bacteriology, 8 ed., (1974), The Williams and Wilkins Company shows that Strain No. C-11924 is similar to *Streptoverticillium cinnamoneum* and *Streptoverticillium hachijoense*. And, for comparison's sake, we cultivated on various media the present strain along with the known strains available from the Institute for Fermentation, Osaka, namely *Streptoverticillium cinnamoneum* IFO-12852 (ISP 5005), *Streptomyces cinnamomeus f. azacoluta* IFO-12363 (*Streptoverticillium cinnamoneum f. azacoluta*) and *Streptomyces hachijoensis*, IFO-12782 (ISP 5114) (*Streptoverticillium hachijoense*). As will be seen from Table 4, Strain No. C-11924 bears a close resemblance with these three strains of microorganisms in the color of aerial mycelium, physiological characters, carbon utilization spectrum, etc. However, *Streptomyces hachijoensis* differentiates itself from Strain No. C-11924 in that the former cannot grow on glycerol-asparagine agar or tyrosine agar medium. Strain No. C-11924 appears to resemble *Streptomyces cinnamomeus f. azacoluta* more closely in that they have a light yellow to dull yellow substrate mycelium and peptonize milk but this latter strain differentiates itself from Strain No. C-11924 in that it cannot grow on tyrosine agar. Furthermore, Strain No. C-11924 differs from those known organisms in that it gives a light olive aerial mycelium on glycerol nitrate agar. Based on the above findings, we have identified Strain No. C-11924 as a strain of *Streptoverticillium cinnamoneum* and designated it *Streptoverticillium cinnamoneum* No. C-11924.

Table 4

Comparison of Strain No. C-11924 with known species

| Medium | | Strain No. C-11924 | *Streptomyces cinnamomeus f. azacoluta* | *Streptomyces hachijoensis* | *Streptoverticillium cinnamoneum* |
|---|---|---|---|---|---|
| Sucrose nitrate agar | Growth | Poor, colorless | Poor, colorless | Moderate | Poor, colorless |
| | Aerial mycelium | Sparse, light pink | Sparse, light pink | Moderate, light beige | Sparse, light pink |
| | Reverse | Colorless | Colorless | Light beige | Colorless |
| | Soluble pigment | None | None | None | None |
| Glycerol nitrate agar | Growth | Good, creased | Good | Good, creased | Good, limited growth |
| | Aerial mycelium | Moderate, light olive | Abundant, velvety, white with a tinge of pink | Moderate, white with a tinge of beige | Moderate, bright brownish gray |
| | Reverse | Light yellow | Light yellow | Yellowish brown | Brown to dark tan |
| | Soluble pigment | None, or very light yellow | None or very light yellow | None | None |
| Glycerol asparagine agar (ISP-5) | Growth | Moderate, limited growth | Good, creased and raised growth | No growth | Moderate, limited |
| | Aerial mycelium | Abundant, beige with a tinge of pink | Abundant, beige with a tinge of pink | | Moderate, beige with a tinge of pink |
| | Reverse | Light yellow to dull yellow | Dull yellow | | Dark brown |
| | Soluble pigment | None | None | | None |
| Inorganic salts-starch agar (ISP-4) | Growth | Good | Good | Good | Moderate to good |
| | Aerial mycelium | Abundant, velvety; beige with a tinge of pink | Abundant, velvety; beige with a tinge of pink | Abundant, velvety, beige with a tinge of pink | Abundant, beige with a tinge of pink |
| | Reverse | Light yellow | Light yellow | Light yellow | Brown to dark tan |
| | Soluble pigment | None | None | None | None |
| Tyrosine agar (ISP-7) | Growth | Moderate, limited and creased growth | No growth | No growth | No growth |
| | Aerial mycelium | Sparse, whitish to yellow | | | |
| | Reverse | Yellowish brown | | | |
| | Soluble pigment | None | | | |
| Liquefaction of gelatin | | +++ | +++ | +++ | + |
| Peptonization of milk | | +++ | +++ | +++ | − |
| Hydrolysis of starch | | +++ | +++ | +++ | +++ |
| Reduction of nitrates | | − | − | − | − |
| Utilization of carbohydrates | | | | | |
| Mannitol | | ± | ± | ± | − |
| Inositol | | +++ | +++ | +++ | + |
| Glycerol | | +++ | +++ | +++ | ++ to +++ |
| Glucose | | +++ | +++ | +++ | − |
| Arabinose | | ± | ± | ± | − |
| Xylose | | ± | ± | ± | − |
| Rhamnose | | ± | ± | ± | − |
| Fructose | | + to ++ | ++ | + to ++ | + |

Table 4-continued

| Medium | Comparison of Strain No. C-11924 with known species | | | |
|---|---|---|---|---|
| | Strain No. C-11924 | *Streptomyces cinnamomeus f. azacoluta* | *Streptomyces hachijoensis* | *Streptoverticillium cinnamoneum* |
| Raffinose | ± | ± | ± | ± |
| Mannose | +++ | +++ | +++ | ++ |
| Starch | +++ | +++ | +++ | +++ |
| Control | ± | ± | ± | − |

+++: Luxuriant growth
++: Good growth
+: Growth
±: Poor growth
−: No growth

On the other hand, in view of the fact that the novel antibiotic C-11924 produced by Strain No. C-11924 belongs to the phleomycin-bleomycin group of antibiotics, Strain No. C-11924 was compared with the microorganisms known to produce antibiotics of this group.

Thus, Strain No. C-11924 differentiates from *Streptomyces verticillus*, the phleomycin-bleomycin-producing strain described in Journal of Antibiotics 12 A, 111 (1959), 19 A, 200–209 (1966), in that the latter has an aerial mycelium white to gray or gray with a tinge of green. Strain No. C-11924 differs also clearly from the following strains in sporulated hyphae and other morphological features. *Streptomyces flavoviridis* (Japanese Patent Application Laidopen No. 22687/1973); *Streptomyces bikiniensis var. zorbonensis*, the zorbamycin-producing strain described in Journal of Bacteriology 105, 880–885 (1971); *Streptomyces humidus var. antitumoris*, YA-56X and Y-producer as described in Journal of Antibiotics 26, 70–76 (1973); *Streptosporangium violaceochromogenes*, an XK-49-1B-2-producer as described in Japanese Patent Application Laid-open No. 42896/1974; and *Streptomyces olivogriseus*, the SS-70A and B-producing microorganism described in Japanese Patent Application Laidopen No. 15693/1976.

Like other microorganisms of the genus Streptoverticillium, Strain No. C-11924 is liable to change its characters, being ready to undergo mutation when subjected to an artificial mutagenic treatment such as irradiation with ultraviolet light, X-rays or other radiation or with an artificial mutagen. It should be understood than even such mutants can invariably be utilized in the method of this invention only if they are capable of producing C-11924 F-1.

In the method of this invention, the medium for cultivation of Strain No. C-11924 may be whichever of a fluid medium and a solid medium, although fluid media are more convenient. Either surface culture or shaking culture may be carried out, submerged culture being more advantageous. In the medium are incorporated carbon sources which Strain No. C-11924 is able to assimilate, such as starch, glucose, dextrin, glycerin, sucrose, n-paraffin, alcohols (e.g. methanol), etc. and nitrogen sources such as corn steep liquor, soybean flour, cottonseed flour, peptone, meat extract, urea, etc. by way of organic nitrogen sources, or ammonium chloride, ammonium sulfate, ammonium nitrate, etc. by way of inorganic nitrogen sources. If necessary, there may be incorporated appropriate amounts of inorganic salts such as salts including sodium, potassium, magnesium, calcium or phosphorus salts heavy metal salts such as salts of iron, manganese, zinc, cobalt, copper, nickel, etc.; antifoams such as soybean oil, lard oil, chicken oil, silicone oil, Actocol (Takeda Chemical Industries Ltd., Japan), etc. In carrying out a fluid culture, the pH of the medium is preferably maintained near neutral and, particularly, at pH 6 to 8. The incubation temperature and time are preferably 24° C. to 30° C. and 90 to 140 hours, respectively. The change in the titer of activity with the time of cultivation can be monitored by the paper disc method using *Salmonella typhimurium* IFO 12529 as the assay organism (assay medium: Trypticase soy agar, BBL).

C-11924 F-1 as obtainable by this invention is a copper-containing basic peptide antibiotic and can be separated, recovered and purified from the cultured broth by procedures commonly employed. Thus, concentration under reduced pressure, lyophilization, solvent extraction, dialysis, adsorption on activated carbon, silica gel, alumina or the like, or on a synthetic adsorbent of the macroporous nonionic type, e.g. Amberlite XAD-2, Diaion HP-10 or the like, weakly acidic ion exchange resin, gel-filtration agent, ion exchange-gel filtration agent, etc. may be employed in a suitable and optional combination or in repetition.

An exemplary purification procedure may be as follows.

Because C-11924 F-1 occurs in the liquid phase of the cultured broth, the cells are first removed from the cultured broth by means of a filtration aid such as diatomaceous earth and the active component of the filtrate is adsorbed on a column of Diaion HP-10 (Mitsubishi Kasei K.K. in Japan). After a thorough aqueous rinse, the active component is eluted with a mixture of water and one or more hydrophilic solvents such as lower ketones, e.g. acetone, methyl ethyl ketone, or lower alcohols, e.g. methanol, ethanol, isopropanol, n-propanol, n-butanol, etc. The active fractions are concentrated under reduced pressure to remove the organic solvent and the concentrate is subjected to molecular-sieve chromatography on a gel filtration agent. First, using a column of Sephadex LH-20, (Pharmacia Fine Chemicals AB, Sweden), solvent-soluble impurities are removed by development with aqueous alcohol and the active fractions are concentrated under reduced pressure and lyophilized to obtain crude powders. To purify the crude powders, column chromatography with an ion exchange-gel filtration agent is most effective but, because of the basic nature of the substance, CM-Sephadex C-25 will prove most effective. The crude powders are dissolved in a dilute solution of formic acid in ammonia and the solution is adsorbed on CM-Sephadex C-25, elution being carried out with formic acid-ammonia by the gradient method. The active fractions emerging as a single peak at 0.32 to 0.37 mol concentration of formic acid-ammonia are collected and adsorbed on a column of Diaion HP-10. Elution is carried out with aqueous alcohol and the desalted eluate is lyophilized. By this procedure is obtained C-11924F-1 which is paper chromatographically a single substance.

The physical and chemical properties of C-11924F-1 obtained in Example 1 are as follows.

1. Appearance: Blue amorphous powder

| 2. Elemental analysis: | | | |
|---|---|---|---|
| C: | 40.81; | 40.87; | 40.55 |
| H: | 5.72; | 5.02; | 5.55 |
| N: | 16.35; | 16.58; | 16.40 |
| S: | 3.95; | 3.97; | 3.50 |
| Cu: | 3.64; | 3.46; | 3.29 |

3. Melting point (decomp.): not lower than 195° C. (no definite decomposition point)

4. Molecular weight:

(I) Vapor-pressure osmosis: n·($1.0 \times 10^3$)(n is an integer) (distilled water) It is quite within the bounds of possibility that n is 2.

(II) Molecular weight as calculated on the assumption that each molecule contains one atom of copper: 1800±50

5. Ultraviolet absorption spectrum:

As shown in FIG. 1, there are absorption maxima in aqueous solution at 243 nm±2($E_{1\ cm}^{1\%}$ 167±16) and 297 nm±2 ($E_{1\ cm}^{1\%}$ 55±6).

6. Infrared absorption spectrum:

The spectrum obtained by the KBr method is shown in FIG. 2. Principal peaks in the infrared absorption spectrum are as follows ($cm^{-1}$).

3350, 2920, 1715, 1650, 1625, 1600, 1550, 1520, 1450, 1370, 1345, 1090, 1060, 1005, 980

7. Solubility:

Readily soluble in water; soluble in methanol; sparingly soluble in ethanol; insoluble in ethyl acetate, butyl acetate, chloroform, benzene, cyclohexane, ethyl ether and petroleum ether.

8. Color reactions:

Sakaguchi, ninhydrin, Ehrlich, Dragendorff, potassium permanganate and Greig-Leaback reactions are positive.

9. Stability:

Stable under neutral conditions; slightly unstable under alkaline conditions; unstable under acidic conditions 10. Acidity, neturality or basicity: Basic

| 11. | Paper chromatography (ascending method)Rf: | |
|---|---|---|
| | Solvent system | C-11924 F-1 |
| (1) | 50% Acetone water | 0.20 |
| (2) | 75% Phenol | 0.95 |
| (3) | n-Butanol-acetic acid-water (2:1:1) | 0.37 |
| (4) | n-Butanol-pyridine-acetic acid-water (15:10:3:12) | 0.18 |
| (5) | n-Butanol-acetic acid-water (upper layer of 4:1:5 mixture) | 0.13 |
| (6) | 3% Ammonium chloride | 0.82 |

For reference's sake, the corresponding paper chromatographic Rf values of YA-56-X, YA-56-Y, SS-70-A and SS-70-B are given below.

| Solvent system | YA-56-X (Note 1) | YA-56-Y (Note 1) | SS-70-A (Note 2) | SS-70-B (Note 2) |
|---|---|---|---|---|
| (1) | 0.05 | 0.05 | 0.90 | 0.90 |
| (2) | 0.93 | 0.93 | 0.06 | 0.06 |
| (3) | | | | |
| (4) | 0.30 | 0.45 | | |
| (5) | 0.23 | 0.31 | | |
| (6) | | | 0.87 | 0.91 |

Note 1: According to J. Antibiotics 26, 77(1973).
Note 2: According to Japanese Pat. Appl. Laid-open Nos. 15693/76 and 115694/76.

The present antibiotic is compared with the known antibiotics as follows.

Among the known water-soluble copper-containing basic peptide antibiotics are antibiotics of the phleomycin group (Ikekawa et al, Journal of Antibiotics 17 A, 194(1964)), antibiotics of the bleomycin group (Umezawa et al, Journal of Antibiotics 19 A, 200(1966), Zorbamycin, Zorbmycin B, Zorbonomycin C(A.D. Algoudelis et al. Journal of Antibiotics 24, 543(1971); YA-56-X and YA-56-Y(Itoh et al, Journal of Antibiotics 24, 727(1971)); XK-49–1-B-2(Jap. Pat. Appl. Laid-open No. 42896/1974); and SS-70-A and SS-70-B(Jap. Pat. Appl. Laid-open No. 15693/1976).

In view of the fact that whereas the absorbance ratio of C-11924F-1 in its ultraviolet absorption spectrum at 243 nm versus 297 nm is 3.04, the corresponding ratios for bleomycins, phleomycin C, $D_2$ and F, zorbonomycin B and XK-49–1B-2 are in the range of 1.1 to 1.3, C-11924-F-1 is clearly distinguishable from those known antibiotics.

Based on paper chromatographic data as well, C-11924F-1 is found to be different from the known antibiotics.

However, because the ratios for phleomycin $D_1$, E, G, H and I, zorbamycin, YA-56-X, YA-56-Y, SS-70-A and SS-70-B are in the range of 2.7 to 2.9, there is a similarity in this respect. (Incidentally, it is reported in Journal of Antibiotics 26, 77(1973) that YA-56-X and zorbamycin are the same substance). FIG. 3 shows the elution pattern of a mixture of SS-70-B and C-11924F-1 from a chromatographic column of CM-Sephadex C-25. The two components give independent peaks, indicating clearly that they are different substances. As to differences from phleomycin antibiotics, YA-56-X and Y or SS-70-A, while those substances are all eluted in advance of SS-70-B according to the description in Japanese Patent Application Laid-open No. 15694/1976, C-11924 F-1 ermerges after SS-70-B as shown in FIG. 3, thus indicating that the present antibiotic is also distinguishable from those known antibiotics.

It is apparent from the above results that C-11924 F-1 is a novel antibiotic dissimilar to any of the known antibiotics of the bleomycin-phleomycin group.

ANTIMICROBIAL SPECTRUM

The antimicrobial spectrum of C-11924 F-1 as determined by the agar dilution method using Trypticase soy agar as the assay medium (Baltimore Biologicals Limited, U.S.A.) is given in Table 5.

Table 5

| Antimicrobial Spectrum | |
|---|---|
| Assay organism | Minimal inhibitory concentration, mcg/ml C-11924F-1 |
| Staphylococcus aureus FDA 209 P | 2.0 |
| Bacillus subtilis PCI 219 | 1.0 |
| Bacillus cereus IFO 3514 | 20.0 |
| Bacillus pumilus IFO 3813 | >100 |

Table 5-continued

Antimicrobial Spectrum

| Assay organism | Minimal inhibitory concentration, mcg/ml C-11924F-1 |
|---|---|
| *Escherichia coli* NIHJ | 0.2 |
| *Proteus vulgaris* IFO 3045 | >100 |
| *Proteus mirabilis* IFO 3849 | >100 |
| *Pseudomonas aeruginosa* IFO 3080 | >100 |
| *Salmonella typhimurium* IFO 12529 | 0.1 |
| *Alcaligenes faecalis* IFO 13111 | >100 |
| *Mycobacterium* sp. 607 | 0.5 |
| *Aspergillus niger* IFO 4066 | 5.0 |
| *Candida albicans* IFO 0583 | >100 |

TOXICITY

The acute toxicity $LD_{50}$ in mice as intravenously dosed is about 200 mg/kg.

As shown by the antimicrobial spectrum given above, C-11924 F-1 according to this invention is highly active against gram-negative bacteria, gram-positive bacteria, mycobacteria and fungi and is a useful substance displaying potent germicidal activity. For instance, the present antibiotic is also of value as germicides and disinfectants against pathological microorganisms similar to the above-mentioned assay organisms.

Since the present antibiotic has therapeutic effects in mice infected with *Escherichia coli,* it is also an effective agent for use in the management of mammalian cases (e.g. mouse, rat, man) infected with the abovementioned bacteria.

To employ C-11924F-1 as a germicide-disinfectant, it can be used, for example, as a liquid preparation containing 5 to 200 μg per ml, the concentrations depending upon the intended application. C-11924 F-1 may also be used as an ointment, for example by admixing 50 mg of it thoroughly with 10 g of petrolatum album.

C-11924 F-1 is subcutaneously administered in a form of injection liquid which is prepared by dissolving C-11924 F-1 in water or physiological saline. The daily dosage as C-11924 F-1 is 5 to 30 mg/kg.

When administered to mice inoculated with Sarcoma 180 ascites-tumor cells, C-11924 F-1 strongly inhibits the multiplication of tumor cells and has potent life-span extending effects. Therefore, C-11924 F-1 is also useful as an antitumor agent for the treatment of Sarcoma 180 ascites tumor cells in mice.

The following examples are intended to describe this invention in further detail.

In the examples "part(s)" is based on weight unless otherwise noted and the relationship between "part(s)" and "part(s) by volume" corresponds to that between "gram(s)" and "milliliter(s)", and "%" is based on "weight/volume" unless otherwise noted.

EXAMPLE 1

Fermentation tanks with 2000 part by volume capacity were each filled with 500 parts by volume of a medium made up of 3% of soluble starch, 2% of glucose, 1% of raw soybean meal, 1% of corn steep liquor, 0.5% of peptone, 0.3% of sodium chloride and 0.5% of calcium carbonate (pH 7.0). The tanks were sterilized and, then, inoculated with *Streptoverticillium cinnamoneum* No. C-11924(IFO 13713; FERM receipt number 3837; ATCC-31364), followed by cultivation on a reciprocating shaker at 28° C. for 40 hours. One thousand five hundred parts by volume of the resultant seed culture was transferred to a tank with 200,000 part by volume capacity tank containing 100,000 parts by volume of a medium composed of 3% of glucose, 2% of soluble starch, 2% of Proflo (Traders Oil Mill Company), 0.5% of peptone, 0.3% of sodium chloride and 0.5% of calcium carbonate (pH 7.0), followed by cultivation with stirring under aerobic conditions and at 28° C. for 90 hours (100 V/V % aeration, 200 r.p.m.).

To 80,000 parts by volume of the cultured broth obtained above was added 1,500 parts of diatomaceous earth as the filtration aid and the mixture was filtered under reduced pressure to obtain 66,000 parts by volume of solution. This solution (pH 7.5) was passed onto a column packed with 7,500 parts by volume of Diaion HP-10 (Mitsubishi Kasei Kogyo K.K., in Japan), whereby the active portion was adsorbed on the resin. After the column was rinsed with 30,000 parts by volume of water, it was washed with 30,000 parts by volume of 20 V/V % methanol. Elution was carried out by the gradient method using 25,000 parts by volume of 40 V/V % methanol and 25,000 parts by volume of 90 V/V % methanol, and the eluate was collected in fractions of 5,000 parts by volume. C-11924 F-1 was eluted in fractions Nos. 3 to 10. The active fractions were pooled and concentrated under-reduced pressure to remove methanol and the residue was passed through a column packed with 500 parts by volume of Diaion HP-10 for a second time. The column was rinsed with 2,000 parts by volume of water and, then, elution was carried out by the gradient method using 1,500 parts by volume of 40% methanol and 1,500 parts by volume of 90 V/V % methanol. The eluate was collected in fractions of 300 parts by volume, the activity being contained in fractions Nos. 2 to 8. The active fractions were pooled, concentrated under reduced pressure and lyophilized. By this procedure was obtained 17 parts of crude powder.

The crude powder obtained above was purified on a column of Sephadex LH-20. Thus, 10 parts of the crude powder were dissolved in 20 parts by volume of 40 V/V % methanol and, after removal of insolubles, the filtrate was put on a well-rinsed column packed with 900 parts by volume of Sephadex LH-20 which has previously been well-rinsed by 40 V/V % methanol and developed with 40 V/V % methanol. The eluate was collected in 50 parts by volume fractions, the activity being contained in fractions Nos. 9 to 11. By lyophilization, 3.1 parts of crude powder was obtained. The crude powder was dissolved in 200 parts by volume of 0.05 M. ammonium formate and adsorbed on a column packed with 130 parts by volume of CM-Sephadex C-25. The column was washed with 200 parts by volume of 0.1 M. ammonium formate and elution was carried out by the gradient method using 1,000 parts by volume of 0.1 M. and 1,000 parts by volume of 1.0 M. ammonium formate. The active substance was eluted in fractions corresponding to 0.32 M. to 0.37 M ammonium formate. The eluate was adsorbed on a column packed with 30 parts by volume of Diaion HP-10, which was thoroughly rinsed with water. Then, elution was carried out with 20 V/V % methanol and, after this desalting, the eluate was lyophilized to recover 0.046 part of a pure blue product of C-11924F-1.

Figure 1:
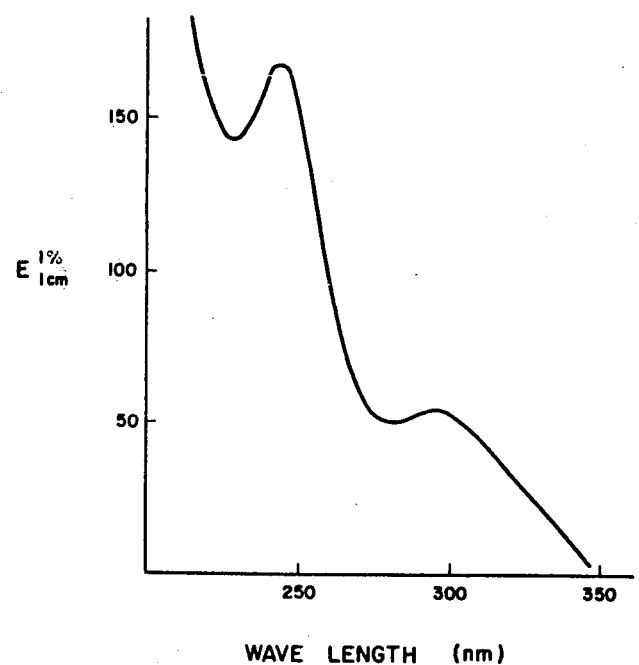
FIG. 1 is an ultraviolet absorption spectrum of C-11924 F-1 (as measured in $H_2O$).
Figure 2:
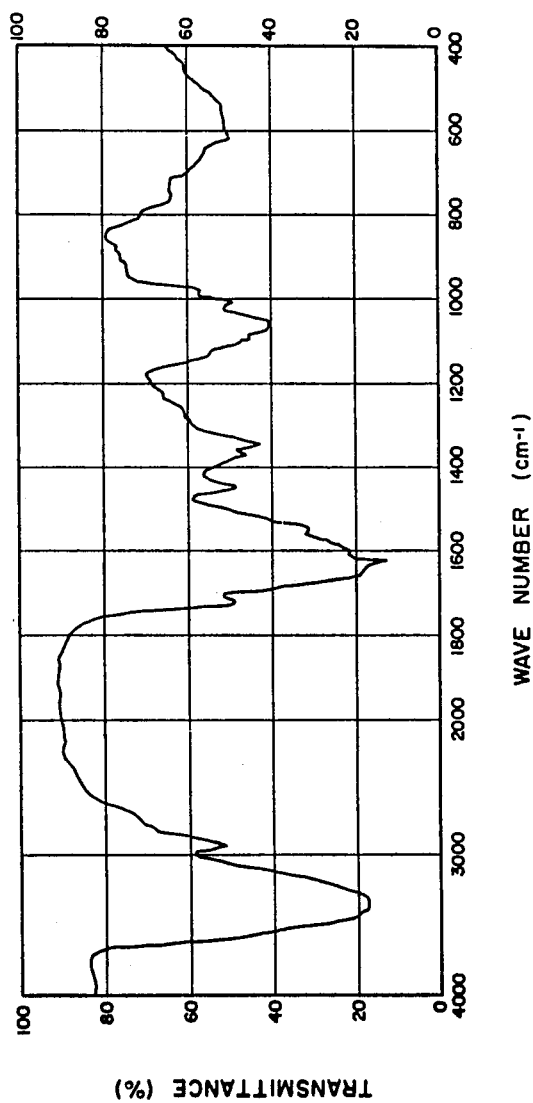
FIG. 2 is an infrared absorption spectrum of C-11924 F-1 (KBr).
Figure 3:
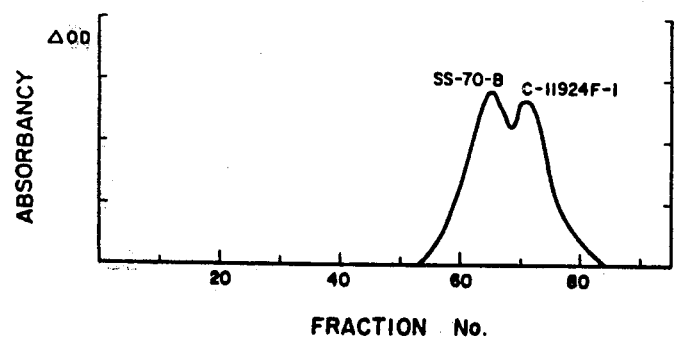
FIG. 3 is a chromatogram of C-11924 F-1 and SS-70-B as determined by CM-Sephadex C-25(H+) and 0.1 M sodium chloride as the developer.

What we claim is;

1. Antibiotic C-11924 F-1 which has the following physico-chemical properties:

| (a) Elemental analysis: |
| --- |
| C, 40.81, 40.87, 40.55 |
| H, 5.72, 5.02, 5.55 |
| N, 16.35, 16.58, 16.40 |
| S, 3.95, 3.97, 3.50 |
| Cu, 3.64, 3.46, 3.29 |

(b) Melting point (decomp.): not lower than 195 degrees centigrade (no definite decomposition point)

(c) Molecular weight: $n \cdot (1.0 \times 10^3)$ (n is an integer) (distilled water, vapor pressure osmosis); $1800 \pm 50$ (as calculated on the assumption that each molecule contains one atom of copper)

(d) Ultraviolet absorption spectrum: $\lambda_{max}^{H_2O} 243 \pm 2$ nm ($E_1 cm^{1\%} 167 \pm 16$) $\lambda_{max}^{H_2O} 297 \pm 2$ nm ($E_1 cm^{1\%} 55 \pm 6$)

(e) Infrared absorption spectrum (KBr)cm$^{-1}$: 3350, 2920, 1715, 1650, 1625, 1600, 1550, 1520, 1450, 1370, 1345, 1090, 1060, 1005, 980

(f) Solubility: Readily soluble in water; soluble in methanol; sparingly soluble in ethanol; insoluble in ethyl acetate, butyl acetate, chloroform, benzene, cyclohexane, ethyl ether and petroleum ether.

(g) Color reactions: Positive Sakaguichi, ninhydrin, Ehrlich, Dragendorff, potassium permanganate and Greig-Leaback reactions.

(h) Stability: Stable under neutral conditions; slightly unstable under alkaline conditions; unstable under acid conditions (i) Acidity, neutrality or basicity; a basic substance.

2. A method of producing Antibiotic C-11924 F-1 as defined in claim 1 which comprises cultivating *Streptoverticillium cinnamoneum* having the identifying characteristics of ATTCC No. 31364 in a culture medium containing an assimilable carbon source and a digestible nitrogen source to cause the antibiotic to elaborate, and accumulate in the cultured broth in a substantial amount, and recovering the said Antibiotic C-11924 F-1.

* * * * *